United States Patent
Berberich

(10) Patent No.: US 8,287,577 B2
(45) Date of Patent: Oct. 16, 2012

(54) PIN FOR FIXING AN IMPLANT SUBJECTED TO TENSILE LOAD

(75) Inventor: Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1305 days.

(21) Appl. No.: 11/266,694

(22) Filed: Nov. 3, 2005

(65) Prior Publication Data

US 2006/0129155 A1 Jun. 15, 2006

(30) Foreign Application Priority Data

Nov. 3, 2004 (DE) .......................... 10 2004 053 471

(51) Int. Cl.
*A61B 17/00* (2006.01)
(52) U.S. Cl. ...................................... 606/329
(58) Field of Classification Search .................. 606/329, 606/300, 309, 321, 86 R; 623/13.12
See application file for complete search history.

(56) References Cited

U.S. PATENT DOCUMENTS

| 5,480,403 | A | 1/1996 | Lee et al. | 606/72 |
| 6,280,474 | B1 | 8/2001 | Cassidy et al. | 623/16.11 |
| 6,632,235 | B2 * | 10/2003 | Weikel et al. | 606/192 |
| 8,088,128 | B2 * | 1/2012 | May et al. | 606/64 |
| 2001/0053934 | A1 | 12/2001 | Schmieding | 623/13.14 |

FOREIGN PATENT DOCUMENTS

| AU | 767 853 | 11/2003 |
| EP | 1 180 351 | 2/2002 |
| EP | 1 297 799 | 4/2003 |
| WO | WO 90/12550 | 11/1990 |
| WO | WO 99/15095 | 4/1999 |
| WO | WO 02/091928 | 11/2002 |
| WO | WO 2004/062459 | 7/2004 |

OTHER PUBLICATIONS

European Search Report; Mar. 29, 2006; 6 pages, of EP 05 02 3512.

* cited by examiner

*Primary Examiner* — Eduardo C Robert
*Assistant Examiner* — David Comstock
(74) *Attorney, Agent, or Firm* — St. Onge Steward Johnston & Reens LLC

(57) ABSTRACT

A pin for fixing an implant subjected to tensile load, in particular a tendon implant, having a rod-shaped body is provided. A force exerted by the implant is input onto the cross section of the body, on one side, and is output on the opposite side to an anchoring site. The cross section of the body has, on the force output side, at least two contact sites via which the input force can be output in a distributed manner. This configuration allows the pin to withstand high tensile loads without fracturing.

5 Claims, 2 Drawing Sheets

PIN FOR FIXING AN IMPLANT SUBJECTED TO TENSILE LOAD

PRIOR APPLICATIONS

This application claims priority of German Patent Application No. 10 2004 053471.3 filed on Nov. 3, 2004.

FIELD OF THE INVENTION

The invention relates to a pin for fixing an implant subjected to tensile load, in particular a tendon implant, said pin having a rod-shaped body, a force exerted by the implant being able to be input onto a cross section of the pin, on one side, and being able to be output on an opposite side to an anchoring site.

BACKGROUND OF THE INVENTION

Pins of this kind are used to fix an implant fitted in an opening in a bone. To do this, the implant is first pushed into the opening, in most cases a bore that has been formed from the outside. The pin is then driven in transversely thereto, thus passing transversely through the bore and through the implant pushed into the latter, as a result of which said implant is fixed in position. Since the pin extends transversely with respect to the longitudinal extent of the implant, the expression "cross pin" has become established.

A common application is in fixing an implant serving as a replacement for the cruciate ligaments of the knee.

For replacing the cruciate ligament, an operating technique has been developed in which the implant or graft, in most cases a tendon from the patient, is formed into a loop, and the cross pin is driven transversely through it in the area of the loop. It is also known for two loose ends of tendon sections to be sewn together. When moving the knee a strong tension acts on the tendon implant which is transferred to the pin.

The tendon loops round the rod-shaped body of the pin in a cross-sectional plane. The result of this is that the tensile load exerted by the tendon is input into the rod-shaped body on one side of its cross section and can be output on the opposite side to anchoring sites which are axially spaced apart from the input side. This anchoring site is the inner wall, geometrically speaking a surface line of the wall, of a bore in which the cross pin is received.

Such pins usually have a circular cross section so that the force output site lies along a surface line of the rod-shaped body lying opposite the loop or cross-section side around which the loop is guided. Additionally, the force input side is located in the central section of the pin, the force output sides are located at the opposite end sections of the pin resting in the bone.

In the event of loading, this has the effect that the force input by the tendon implant is output to the anchoring site in a more or less limited area on the end sections of the pin.

A study has established that this geometry can cause the cross pin to fracture.

In order to remedy this situation, it was attempted to introduce a second identical cross pin, with a likewise circular cross section, directly below the first cross pin in the direction of the force input.

A further study has now shown that even the placement of a second adjacent cross pin is unable to exclude the possibility of fracturing. On the contrary, if the first cross pin fractures under strong tensile loading, then the second cross pin also fractures thereafter. There is, as it were, a kind of domino effect.

It is therefore an object of the present invention is to remedy this situation and make available a pin of the aforementioned type for fixing an implant subjected to tensile load, which pin is able to withstand high tensile loads without fracturing.

SUMMARY OF THE INVENTION

According to the invention, this object is achieved by the fact that the cross section of the pin has, on the force output side, at least two contact sites via which the input force can be output in a distributed manner.

Tests have shown that, with such a geometry, the force input from the tendon on one side can be output in a distributed manner at the at least two contact sites.

With suitable symmetrical geometry, a force F, which is input on one side, is therefore output as F/2 distributed across the two contact sites. It was found that the force output site is a decisive criterion responsible for fracturing in cross pins of circular cross section. With the now at least two contact sites at the force output side, a cross-section geometry is provided which has a higher fracture resistance while having otherwise more or less the same external dimensions.

Seen in the longitudinal direction of the pin, the two contact sites present in the cross section lead to corresponding bridges extending over the entire length of the pin, such that, seen over the entire length of the body of the pin, the corresponding several contact sites for force output are then present.

In a further embodiment of the invention, the cross section has a roughly kidney-shaped configuration.

This measure has the advantage that a mechanically very stable and compact body is present which on one side, that is to say the back of the kidney, offers a suitably large contact surface for the implant, that is to say the side on which the force acts.

In a further embodiment of the invention, the contact sites are designed as cross section projections.

This measure has the advantage that, in this embodiment, corresponding cross sections, seen in the longitudinal direction, corresponding bridges or beads protrude which, for the particular application, can have a suitable geometry and a suitable number so that, with the thinnest possible geometry of the rod-shaped body, it is possible to form optimal force output sites, which contribute to the stability against fracturing.

As before, it is sought to configure the cross pin with the smallest possible cross-sectional dimension in order to keep to a minimum the cross section of the necessary bores in the bone into which the cross pin is to be driven. This not only means that the bone is weakened to the least possible extent but also ensures the quickest possible incorporation of the pin and means that, in the case of absorbable materials, the hollow space formed by absorption of the material is as small as possible.

In a further embodiment of the invention, the cross section projections are rounded.

This measure has the advantage that the cross sections can engage with the anchoring site, in most cases a bone surface of a bore, over a relatively large circumference area, and, as a result of the rounded formation, this engagement is also particularly non-traumatic.

In a further embodiment of the invention, three contact sites are present.

This measure has the advantage that the input force can be output divided in three via the three contact sites, which results in particularly good stability against fracturing.

In a further embodiment of the invention, the cross section has a greater linear dimension in the direction of force input than it has transverse to the direction of the force input.

This measure leads to oval cross sections whose longer axis extends in the direction of the force input. This additionally contributes to the mechanical stability and thus to the resistance to fracturing.

It will be appreciated that the aforementioned features and those still to be discussed below can be used not only in the respectively cited combination, but also in other combinations, or singly, without departing from the scope of the present invention.

DETAILED DESCRIPTION OF THE INVENTION

Figure 1:
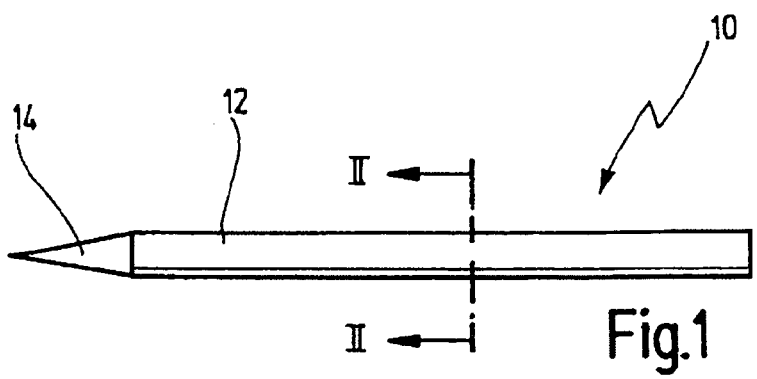
FIG. 1 shows a pin in a side view.
Figure 2:
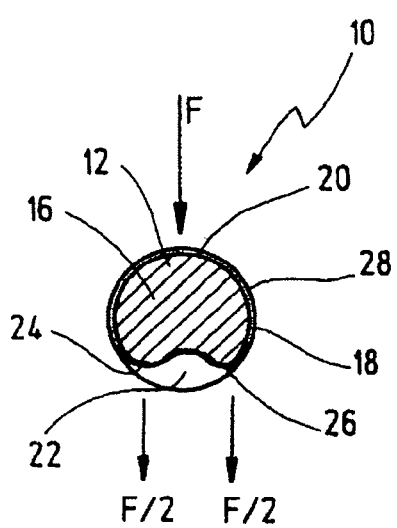
FIG. 2 shows a cross section along the line II-II in FIG. 1.

A pin 10 shown in FIGS. 1 and 2 has a rod-shaped body 12 which, at one end, merges into a conically tapering tip 14.

It will be seen from the view in FIG. 2 that the rod-shaped body 12 has a cross section 16 which has roughly the shape of a kidney 18. The circumferential contour is such that one side 20 is in the shape of an arc of a circle and, on the opposite side 22, two arc-shaped contact sites 24 and 26 are formed.

Seen in the longitudinal direction of the rod-shaped body 12, this can be expressed in terms of a recess or groove being hollowed out. The cross pin 10 has, for example, a length of 40 mm and a diameter of approximately 4 mm.

The pin can be made of absorbable materials, from plastic material or from metal, for example titanium or a titanium alloy.

FIG. 2 shows how the pin 10 is fitted into a bore 28 of circular cross section.

If a force F now acts on the rod-shaped body 12 at an input side, specifically transverse to the longitudinal axis of the pin, that is to say in the direction roughly of a diameter of the pin, then it is apparent that the force F is output via the two contact sites 24 and 26 in each case as F/2 into the material surrounding the bore, for example into a bone material into which the pin 10 is inserted, as will be described later in connection with FIG. 5.

This force output via two contact sites contributes considerably to the stability against fracturing.

Figure 3:
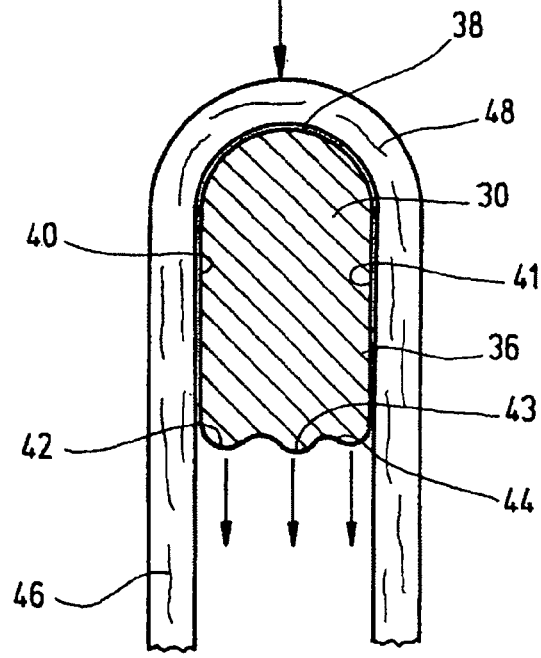
FIG. 3 shows, on a slightly enlarged scale, a cross section, corresponding to FIG. 2, of another illustrative embodiment of a pin with three contact sites and of oval shape, the figure also indicating a tendon implant which is to be fixed by the pin.

FIG. 3 shows a pin 30 which likewise has a rod-shaped body (not shown here) with a conical tip, and which has a cross section 36. The cross section 36 has, on one side, which is the force input side, a semicircle profile 38 which, at the end opposite to the semicircle 38, merges into three projecting contact sites 42, 43 and 44 via two parallel sides 40 and 41.

FIG. 3 shows how a loop 48 of a tendon implant 46 is placed about the cross section 36, specifically in such a way that the loop 48 is placed around the semicircle 38.

In practical use, the tendon implant 46 is subjected to tensile load such that the force acts in the direction of the arrow, that is to say in the direction from the semicircle 38 toward the three contact sites 42, 43 and 44.

There, the force F is then output, divided in three, from the three contact sites 42, 43 and 44.

It will also be seen that the cross section 36 has a greater extension in the direction of the force input than it has transverse to this direction, that is to say also transverse to the longitudinal direction of the rod-shaped body of the pin 30. This not only has the effect, as can be seen from FIG. 3, that the tendon implant bears flat on the pin 30 about a large circumference angle, which promotes incorporation, but also that, as a result of this roughly oval geometry, a particularly good stability is obtained in this force input direction, which in the final analysis additionally contributes to the safety against fracturing.

Figure 4:
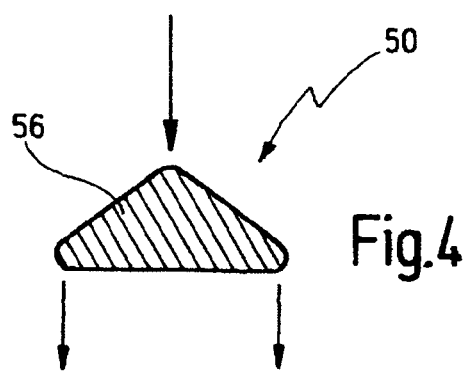
FIG. 4 shows a sectional view, comparable to the view in FIG. 2, of another cross-sectional profile of a pin.

FIG. 4 shows a further pin 50 with an approximately triangular cross section 56. The force acting on the tip of the triangle is distributed over the base of the triangle at the output side.

Figure 5:
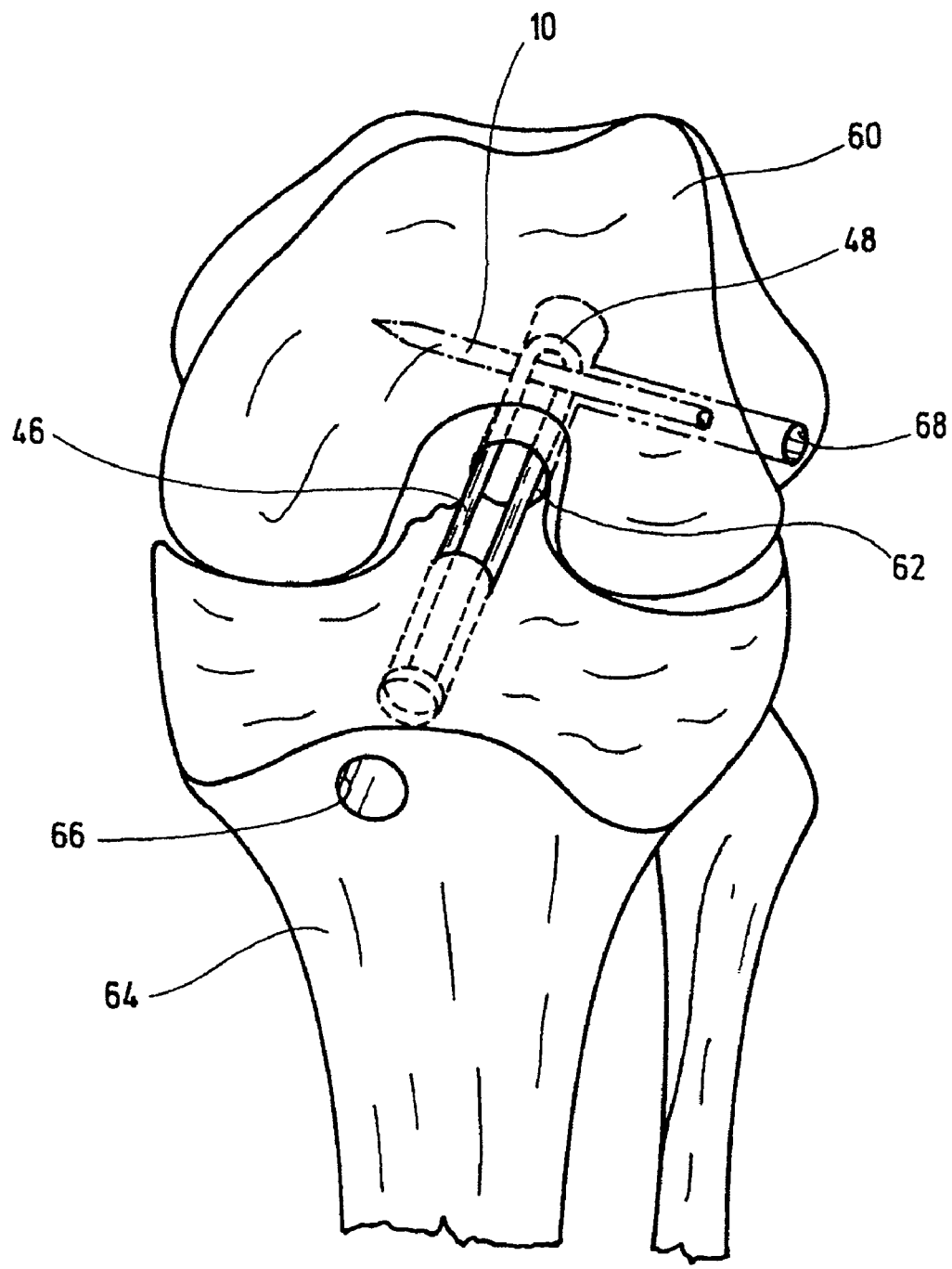
FIG. 5 shows a highly schematic representation of a pin from FIG. 1 which is fitted in a femur for transfixing an implant subjected to tensile load.

FIG. 5 shows a situation in which the pin 10 is used for fixation of a tendon implant 46 serving as a replacement for the cruciate ligament of a human knee.

For this purpose, a through-bore 66 has been formed in the tibia 64 and continues as a blind bore 62 in the femur 60.

A transverse bore 68 has also been formed in the femur 60. This transverse bore 68 transversely passes the blind bore 62 in the femur 60 and allows the pin 10 to be driven in, specifically in such a way that it extends through the loop 48 of the tendon implant 46 which was previously inserted into the blind bore 62. The operating technique and the necessary instruments for forming the bores 62 and 66 and for correctly forming the bore 68 and for fitting and securing the implant and the cross pin are described in particular in U.S. 2003/0065391 A1 and in U.S. Pat. No. 5,601,562, which are incorporated into the specification by reference.

As can be seen from FIG. 5, pin 10 rests in transverse bore 68 extending transversely to blind bore 62. A surface line of transverse bore 68 onto which the rod-shaped body of pin rests represents the anchoring site of pin 10. The tensile load exerted onto pin 10 by the tendon implant 46 in a direction of through-bore 66 in the tibia 64 is distributed via the two contact sites 24 and 26 (see FIG. 2) into the wall of the transverse bore 68.

In the embodiment of FIG. 5 transverse bore 68 extends from the outside of femur 60 up to blind bore 62. When inserting the pin 10 into transverse bore 68 with a respective tool, the pin 10 is driven beyond the blind bore 62 into the bone material of femur 60 like a nail. It is also possible to provide transverse bore 68 in that it extends beyond the blind bore 62.

If a pin 30 of oval cross section is to be fitted, a drill is first used to form the transverse bore 68 with a round cross section, and a dilator with approximately the same contour as the cross pin 30 is then driven in. The dilator is slightly smaller than the cross pin 30 to ensure that a press fit is obtained when the cross pin 30 is introduced.

What is claimed is:

1. A pin for fixing an implant subjected to tensile load, comprising;
    a straight rod-shaped body extending over its total length, from a distal tip to a proximal end, said straight rod-shaped body having a cross-section, a force input side, a force output side, a cross-section plane where an input force is applied, and an anchoring site, said anchoring site being axially spaced apart from said cross-section plane, wherein said cross-section of said straight rod-shaped body has over its total length, on said force output side, at least two contact sites extending from said distal tip to said proximal end for contacting said anchoring site of said pin, said input force being output in a distributed manner via said at least two contact sites, and wherein said cross-section of said straight rod-shaped body has over its total length extending from said distal tip to said proximal end, on a force input side a semi-circular profile merging into said at least two contact sites via two parallel sides.

2. The pin of claim 1, wherein said two contact sites are designed as cross-section projections.

3. The pin of claim 2, wherein said projections of said cross-section are rounded.

4. The pin of claim 1, wherein three contact sites are present.

5. The pin of claim 1, wherein said cross-section has a greater linear extension in a direction of a force input than it has transversed to said direction of said force input.

* * * * *